(12) United States Patent
Lynn et al.

(10) Patent No.: US 11,521,734 B2
(45) Date of Patent: Dec. 6, 2022

(54) RECIPE GENERATION BASED ON NEURAL NETWORK

(71) Applicant: Journey Foods Inc., Chicago, IL (US)

(72) Inventors: Riana Lynn, Evanston, IL (US); Carol Schmitz, Chicago, IL (US)

(73) Assignee: Journey Foods Inc., Austin, TX (US)

( * ) Notice: Subject to any disclaimer, the term of this patent is extended or adjusted under 35 U.S.C. 154(b) by 0 days.

(21) Appl. No.: 17/318,640

(22) Filed: May 12, 2021

(65) Prior Publication Data

US 2021/0265036 A1    Aug. 26, 2021

Related U.S. Application Data (63) Continuation of application No. PCT/US2019/059467, filed on Nov. 1, 2019.

(60) Provisional application No. 62/760,113, filed on Nov. 13, 2018.

(51) Int. Cl.
*G16H 20/60* (2018.01)
*G06N 3/08* (2006.01)
*G06Q 30/02* (2012.01)

(52) U.S. Cl.
CPC .............. *G16H 20/60* (2018.01); *G06N 3/08* (2013.01); *G06Q 30/0282* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,647,121 B1* | 2/2014 | Witlin | ................ | G09B 19/0092 434/127 |
| 2002/0106121 A1* | 8/2002 | McClanahan | .......... | H04N 1/603 382/156 |
| 2010/0292998 A1* | 11/2010 | Bodlaender | ............ | G16H 20/60 705/2 |
| 2011/0123964 A1* | 5/2011 | Aronis | ................... | G16H 20/60 434/127 |
| 2013/0149679 A1 | 6/2013 | Tokuda et al. | | |
| 2014/0244526 A1* | 8/2014 | Georges | ................ | G06Q 50/12 705/317 |

(Continued)

OTHER PUBLICATIONS

Marshall, Jermaine, "Foodpollo: Driving reliable food recommendations from a massive online food portal", University of Notre Dame, ProQuest Dissertations Publishing, 2017 (Year: 2017).*

(Continued)

*Primary Examiner* — Amber A Misiaszek
(74) *Attorney, Agent, or Firm* — Foley & Lardner LLP (57) ABSTRACT

An illustrative aspect of the present disclosure is a system and method of generating a recipe, which includes determining rankings for a plurality of food ingredients for a target food product according to at least one of a health-based feature, a cost, or a prevalence of the plurality of food ingredients. A neural network can receive, as inputs, the rankings of the plurality of food ingredients, and a plurality of existing recipes for food products in a same category as the target food product. The neural network can generate, as output, according to the rankings of the plurality of food ingredients and the plurality of existing recipes, a new recipe for the target food product that incorporates a select food ingredient from the plurality of food ingredients.

20 Claims, 6 Drawing Sheets

(56) References Cited

U.S. PATENT DOCUMENTS

2014/0324899 A1   10/2014  Sherman et al.
2016/0103839 A1*  4/2016  Altaf .................. G06Q 30/0282
                                                      707/723
2017/0220558 A1*  8/2017  Pinel ..................... G06F 40/211
2017/0372197 A1*  12/2017  Baughman .............. A23L 33/30

OTHER PUBLICATIONS

International Search Report and Written Opinion of the International Searching Authority on PCT/US2019/059467 dated Jan. 13, 2020 (14 pages).
International Preliminary Report on Patentability for PCT Appl. Ser. No. PCT/US2019/059467 dated May 27, 2021 (12 pages).

* cited by examiner

```
┌─────────────────────────────────────────────────────────────┐
│ Determine rankings for food ingredients for a target food product │
│           according to one or more features.                │
│                         410                                 │
└─────────────────────────────────────────────────────────────┘
                              │
                              ▼
┌─────────────────────────────────────────────────────────────┐
│   Receive the rankings of the food ingredients and existing food │
│              recipes for food products.                     │
│                         420                                 │
└─────────────────────────────────────────────────────────────┘
                              │
                              ▼
┌─────────────────────────────────────────────────────────────┐
│ Generate, according to the rankings of the food ingredients and │
│  the existing recipes, a new recipe for the target food product │
│                         430                                 │
└─────────────────────────────────────────────────────────────┘
```

RECIPE GENERATION BASED ON NEURAL NETWORK

CROSS-REFERENCE TO RELATED APPLICATION

The present application is a continuation of and claims the benefit of priority to International Application No. PCT/US2019/059467, filed on Nov. 1, 2019 and designating the United States, which application claims priority under 35 U.S. § 119(e) from U.S. Provisional Application No. 62/760,113, filed Nov. 13, 2018, titled "PROVIDING PRECISE NUTRITION SOLUTIONS USING MACHINE LEARNING AND ORGANOLEPTIC TARGETING," the entire contents of which are incorporated herein by reference for all purposes.

FIELD OF DISCLOSURE

The present disclosure is generally related to food products, including but not limited to a system and method for generating recipes for food products based on a neural network.

BACKGROUND

Over 71% of consumers say they eat at least one shelf-stable (more than 4-weeks of shelf-life) snack per day. 77% of people under 35 reported needing snacks to get through the day, and, across all age groups, the majority of surveyed consumers wanted healthier snack options. Plant-based snacking is becoming even more prevalent, with veganism increasing by 600% in the US in the last four years alone, mirroring similar global trends. Likewise, there is a growing demand for functional products. All of these shifts demand that functional foods begin taking over more of the market share for shelf-stable products.

Similarly, large amounts of processed sugars can lead to chronic health issues, such as heart disease and diabetes, and can contribute to obesity, a rising epidemic in the United States in particular. According to a 2017 Obesity Report released by the Organization for Economic Cooperation and Development, over 38% of Americans were overweight or obese, nearly twice the international average. Finding healthy, convenient snacking alternatives to both fresh fruit, which can be challenging to transport, and unhealthy snacks, like fruit snacks, poses a dire need in the snacking industry, especially as trends toward snacking and surrounding types of snacks people want begin to shift.

SUMMARY

Some embodiments include an artificial intelligence (AI) driven platform where customers can manage existing recipes (e.g., upload their product portfolio which can include existing recipes) and leverage ingredient insights, to create novel recipes that target their desired specifications. The AI driven platform can generate food formulations for given inputs of nutritional properties and/or functional benefits (collectively, health-based features), as well as textures, shelf-stability, affordability, etc. Some embodiments create a ranking that helps categorize and/or streamline the product selection.

An illustrative aspect of the present disclosure is a method of generating a recipe, including determining rankings for a plurality of food ingredients for a target food product according to at least one of a health-based feature, a cost, or a prevalence of the plurality of food ingredients, receiving, by a neural network as inputs, the rankings of the plurality of food ingredients, and a plurality of existing recipes for food products in a same category as the target food product, and generating, by the neural network as output, according to the rankings of the plurality of food ingredients and the plurality of existing recipes, a new recipe for the target food product that incorporates a select food ingredient from the plurality of food ingredients.

Another illustrative aspect of the present disclosure is a system for generating a recipe, including a storage device configured to store a database of a plurality of food ingredients for a target food product, at least one processor configured to determine rankings for the plurality of food ingredients for the target food product according to at least one of a health-based feature, a cost, or a prevalence of the plurality of food ingredients, and a neural network implemented by the at least one processor. The neural network is configured to receive as inputs the rankings of the plurality of food ingredients, and a plurality of existing recipes for food products in a same category as the target food product, and generate as output, according to the rankings of the plurality of food ingredients and the plurality of existing recipes, a new recipe for the target food product that incorporates a select food ingredient from the plurality of food ingredients.

In some embodiments, the system and method include receiving, by the neural network as another input, properties of each of the plurality of food ingredients, and generating, by the neural network, according to the rankings of the plurality of food ingredients, the plurality of existing recipes and the properties of each of the plurality of food ingredients, the new recipe. In some embodiments, the new recipe has a higher probability of incorporating a first food ingredient than a second food ingredient with a ranking that is lower than that of the first food ingredient in the plurality of food ingredients, as the select food ingredient.

In some embodiments, the select food ingredient has a ranking that is lower than that of at least one food ingredient in the plurality of food ingredients. In one embodiment, the system and method include tagging a first recipe of the plurality of existing recipes, to limit a type of modification to the first recipe by the neural network in generating the new recipe.

In some embodiments, the target food product comprises at least one of: a snack, a baked food, a confectionery, a synthetic plant-based product, an energy bar, a beverage, a meal substitute, a dietary supplement, a superfood, a beverage, a shelf-stable food, a frozen or refrigerated food, a meat based product, or a dairy product. In one embodiment, the system and method include generating, by the neural network, the new recipe for the target food product that incorporates multiple food ingredients from the plurality of food ingredients. In one embodiment, the system and method include generating, by a label engine, a nutritional description for the new recipe.

In one embodiment, determining the rankings includes determining first rankings for the plurality of food ingredients according to at least one health-based feature of each of the plurality of food ingredients, determining second rankings for the plurality of food ingredients according to a cost of each of the plurality of food ingredients, determining third rankings for the plurality of food ingredients according to a prevalence of each of the plurality of food ingredients, and determining the rankings for the plurality of food ingredients according to the first rankings, the second rankings and the third rankings.

Both the foregoing summary and the following description of the drawings and detailed description are illustrative and explanatory. They are intended to provide further details of the inventive concepts, but are not to be construed as limiting. Other objects, advantages, and novel features will be readily apparent to those skilled in the art from the following detailed description of the inventive concepts.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing.

DETAILED DESCRIPTION

Before turning to the figures, which illustrate certain embodiments in detail, it should be understood that the present disclosure is not limited to the details or methodology set forth in the description or illustrated in the figures. It should also be understood that the terminology used herein is for the purpose of description only and should not be regarded as limiting.

Most food products currently on the market use a large amount of sugar and additives for texture and taste. Solutions exist for generating recipes for healthier food options but the existing solutions have severe limitations. The existing solutions may be based upon isolated data or historical data, limiting the likelihood that the food product aligns with current market trends for food properties such as flavor and texture. Moreover, the existing solutions may include manual generation of recipes for food products, resulting in additional delay in generating the recipe, and ultimately, getting the food products on the shelf faster. Accordingly, there is a technical problem to automate the exploration, prototyping and/or generation of novel recipes for healthier, flavorful food products.

Some embodiments of the present disclosure offer a technical solution to the technical problem. That is, some embodiments of the present disclosure are a system and method for generating food product recipes using artificial intelligence or machine learning (e.g., neural network) models. In some embodiments, the system and method ranks food ingredients. In some embodiments, the food rankings are based on ingredient properties and/or defined (e.g., customer or consumer) preferences. In some embodiments, the system and method inputs the ranked food ingredients and existing recipes to the artificial intelligence model. In some embodiments, the artificial intelligence model generates new recipes based on the ranked food ingredients and the existing recipes.

Advantageously, some embodiments of the present disclosure use artificial intelligence (e.g. trained machine learning models) to reduce time to generate and/or develop novel recipes for flavorful food products that are healthier than the food products currently available to the general public. Further, some embodiments of the present disclosure prioritize or rank the food ingredients and generate the new recipes based on current data from various sources, ensuring that the new recipes accurately reflect current market trends regarding flavor and/or texture for instance.

Figure 1:
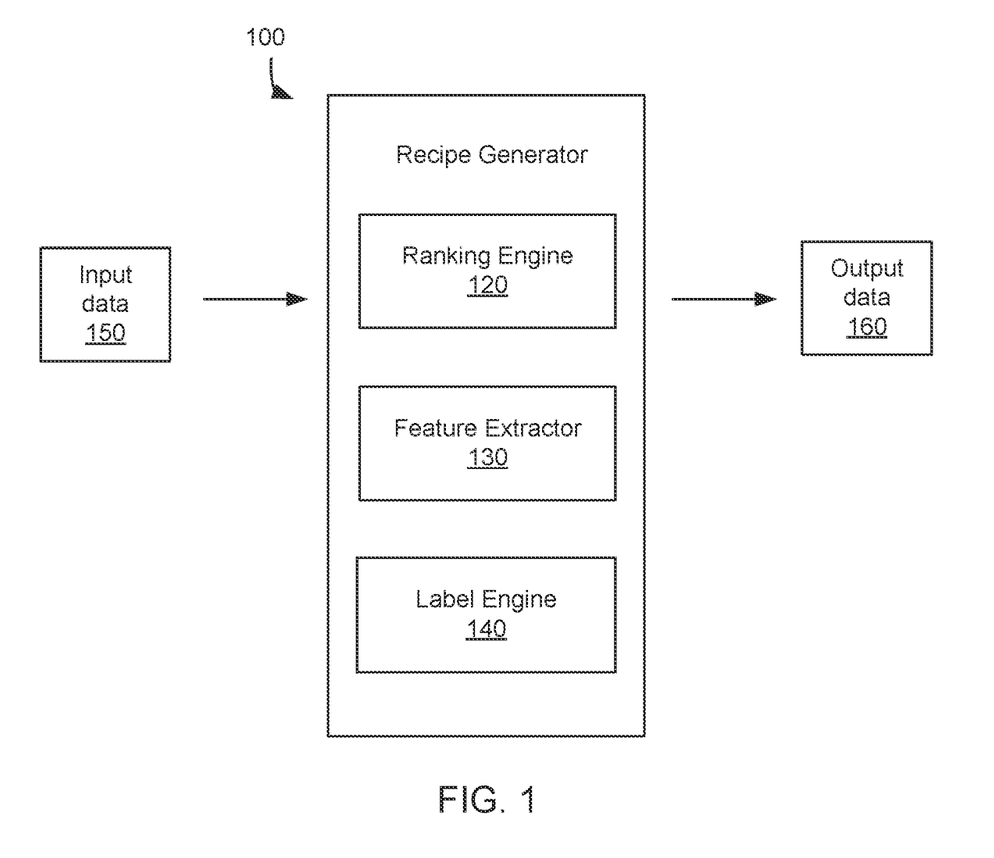
FIG. 1 is a block diagram of a system for generating recipes, according to an example implementation of the present disclosure.

FIG. 1 is a block diagram of a system for developing and/or generating recipes (e.g., recipe generator 100), according to an example implementation of the present disclosure. In some embodiments, the recipe generator 100 includes more, fewer, or different components than shown in FIG. 1. Each of the components may include hardware, or a combination of hardware and software. Each of the components may include or be implemented using one or more elements of the computing system 514 in FIG. 5, and can use these element(s) to perform various operations described herein. In some embodiments, the recipe generator 100 includes a ranking engine 120, a feature extractor 130, and a label engine 140 (collectively, recipe generation components). The recipe generation components may operate together to receive input data 150, e.g., ingredients (e.g., a list of ingredients), ingredient property data (e.g., data indicating health-based features, measures, consistency, texture, flavor, taste, consistency, acidity, color, shelf-life, response to heat or humidity, market data such as cost and/and prevalence, ingredient category, and the like), existing recipe data, customer/consumer/user preference data (e.g., tags, labels, data from feedback, preferences associated with health-based features, cost, and prevalence/availability/popularity), and market data (e.g., research data, data from web scrapes, data associated with cost, prevalence/availability/popularity, recommended daily intake, and the like). Health-based features can include functional features (e.g., having functions and/or characteristics known or believed to be associated with being diabetes-friendly, high fiber, good for treating anxiety, and the like) or nutritional measures (e.g., measures for vitamins, minerals, calories, fats, cholesterol, carbohydrates, proteins, sugars, sodium, and so on). The recipe generation components may operate together to generate (e.g., generate, create, produce, synthesize, provide, determine, calculate, and the like) output data 160 (e.g., ingredient rankings, new recipes, nutritional descriptions, and the like).

In some embodiments, the system includes a ranking engine 120. The ranking engine 120 receives input data 150 (e.g., ingredients, ingredient property data, customer/consumer/user preference data, and the like), in one or more embodiments. The ingredient property data may include an identifier or name of the ingredient, one or more food type indicators (e.g., meat, non-meat protein, dairy, vegetable/vegetarian, fruit, gluten-free, nut-free, or a combination thereof), one or more nutritional values (e.g., values for vitamins, minerals, sodium, sugars, fats, cholesterol, carbohydrates, protein, fiber, and the like, expressed for instance in grams or milligrams per serving, as a percentage of daily recommended value, etc.), one or more functional benefit indicators (e.g., heart, cognitive, metabolism), and/or one or more functional risk indicators (e.g., heart, cognitive, metabolism). The nutritional values can be for a normalized unit of mass (e.g., 100 grams) or weight (e.g., 1 ounce). The ingredient property data, as well as customer/consumer/user preference data, market data, or any other data, can be stored in storage (e.g., cloud storage, local storage, object storage, database, catalog, relational database, associative database, and the like) included in or associated with the system 100.

In some embodiments, the ranking engine 120 filters (e.g., filters, prunes, extracts, keeps, or otherwise maintains) a subset of ingredients from the ingredients based on customer/consumer/user preference data. By way of a non-limiting example, the ranking engine 120 may receive a tag (e.g. a customer tag) indicating that meat-based ingredients are to be excluded from the subset of ingredients. A tag can be in the form of a note, indicator, instruction, guidance, restriction, modifier, setting, parameter, configuration, etc., to drive or control the ranking engine 120. The ranking engine 120 may generate a subset of ingredients excluding ingredients having a food type indicator that indicates presence or use of meat. In some embodiments, the tag may be provided in the form of a phrase, a sentence, a paragraph, and the like, and the ranking engine 120 uses natural language processing (e.g., using a trained neural network or machine learning model) to extract the preference data from the tag. In some embodiments, the ranking engine 120 bypasses filtering such that instead of generating a subset of ingredients, it enables the system to use all of the ingredients.

In some embodiments, the ranking engine 120, or another component such as the feature extractor 130, may classify the ingredients into different ingredient categories (e.g., categories, classes, groups, clusters, and the like). In some embodiments, ingredients of a same ingredient category (e.g., in taste, texture, color, source, shelf-life, response to temperature or humidity, and so on, or any combination thereof) can be swapped for each other (e.g., in a recipe), but ingredients of different ingredient categories cannot be swapped for each other. In some embodiments, the ranking engine 120 or the feature extractor 130 may use an algorithm, program and/or neural network model for classification. The neural network model is described with respect to FIGS. 2A-2B. In some embodiments, upon determining the ingredient category of an ingredient, the ranking engine 120, or another component, adds the ingredient category to the ingredient property data.

In some embodiments, the system includes a ranking engine 120. The ranking engine 120 generates ingredient rankings of the subset of ingredients based on the input data 150, in one or more embodiments. In some embodiments, the ingredient rankings for the subset of ingredients are based on at least one of a health-based feature of the ingredient, a cost of the ingredient (e.g., cost of purchasing, cultivating, producing, sourcing, transporting, storing, maintaining, using and/or processing the ingredient), and/or a prevalence of the ingredient (e.g., prevalence, level of usage/presence and/or popularity of the ingredient in all/similar recipes and/or food products in the market, and/or availability, scarcity or abundance of the ingredient in the market or from sources). In some embodiments, the ranking engine 120 generates an ingredient score for each of the ingredients and generates rankings according to the ingredient scores (e.g., the ingredients are ranked from highest to lowest ingredient scores). In some embodiments, the ranking engine 120 generates a sub-score for each property, or other aspect, of the ingredient (e.g., the flavor, the texture, the cost) and combines or aggregates (e.g., aggregates, sums, adds) the sub-scores to arrive at the ingredient score for the ingredient. In some embodiments, the ranking engine 120 assigns a first score value if the property exceeds a predefined property threshold or a second score value if the property does not exceed the predefined property threshold. The predefined property threshold may be defined by customer/consumer/user preference data. In some embodiments, the predefined property threshold is a specific threshold for the ingredient. In some embodiments, the predefined property threshold is a threshold for any ingredient in the same ingredient category as the ingredient. For example, The ranking engine 120 can determine that the amount of vitamin C provided by an ingredient, apple, is greater than an amount of vitamin C that a customer/consumer/user prefers for any fruit ingredient. The ranking engine 120 can for instance assign a score value of 1 to the ingredient, apple, based on the property data exceeding the customer/consumer/user preference data.

In some embodiments, the sub-scores can be weighted (e.g., weighted, modified, augmented, multiplied, and the like) by data indicating customer/consumer/user preferences. For example, a first customer/consumer/user preference data may indicate that a flavor property has twice the weight of other properties (e.g., texture and cost). In some embodiments, the weighted sub-scores are aggregated or otherwise combined to arrive at the ingredient score. In some embodiments, for each customer/consumer/user preference data element, the ranking engine 120 can assign a value score based on how much the customer/consumer/user preference data element exceeds the associated ingredient data or market data element.

In some embodiments, the ranking engine 120 determines first rankings for the subset of ingredients according to at least one health-based feature of each of the subset of ingredients, second rankings for the subset of ingredients according to a cost of each of the subset of ingredients, and third rankings for the subset of ingredients according to a prevalence of each of the subset of ingredients. In some embodiments, the ranking engine 120 determines the rankings for the subset of ingredients according to the first rankings, the second rankings and/or the third rankings. In some embodiments, the ranking engine 120 determines the ranking for an ingredient by determining a function (e.g., an average, a weighted average, and the like) of the first ranking, the second ranking, and/or the third ranking of the ingredient.

In some embodiments, the ranking engine 120 filters and/or ranks ingredients based on the respective assigned scores. In some embodiments, the order of operations performed by the ranking engine 120 is scoring, filtering, and ranking, for instance. That is, the ranking engine 120 filters ingredients having an ingredient score greater than a predefined threshold score, in some embodiments. The ranking engine can then rank the filtered ingredients. In some embodiments, the order of operations performed by the ranking engine 120 is scoring, ranking, and filtering, for instance. That is, the ranking engine 120 ranks the ingredients having assigned scores. The ranking engine can then filter the ranked ingredients, to identify those having a rank greater than a threshold rank. As an example, the ranking engine determines the threshold rank as the rank associated with the highest ingredient score that is lower than the predefined threshold score, in some embodiments.

The feature extractor 130 includes or corresponds to a component that receives the input data 150 (e.g., the existing recipes, ingredient property data, customer/consumer/user preference data, market data, and the like) and/or the ingredient rankings of the ranking engine 120, in one or more embodiments. In some embodiments, the existing recipes are (selected from a database of recipes for instance, and selected to be) in a same category as a target food product. The target food product can include at least one of a snack (e.g., savory or sweet), a baked food, a confectionery, a synthetic plant-based product, an energy bar, a beverage, a meal substitute, a dietary supplement, a superfood, a bakery fresh product, bakery component(s)/ingredient(s), a dried bakery product, a beverage, a condiment/sauce, a shelf-stable dessert, a dairy product (e.g., milk product, yogurt, cheese, or spreadables), a dessert that is fresh, refrigerated, or frozen), a deli meat product, a fruit/vegetable/produce (e.g., fresh, refrigerated, or frozen) product/blend/salad/cocktail/salsa/sauce, a prepared food or entree (e.g., frozen or refrigerated), a meat/egg/seafood (e.g., fresh, refrigerated, or frozen), a shelf stable prepared food or entree, a tincture, a pill or supplement, a breading, a fruit snack, a bar, a chip, a cracker, a cookie, an ice cream, a popcorn product, a pudding, a pasta, a cereal product, a syrup, a soft drink, a biscuit, a tortilla, a batter, a candy (e.g., chocolate or non-chocolate), a tofu product, a drink mix, a salad dressing, a muffin, a waffle, a noodle product, a burger patty, a taco, a jam or spread, a sauce, a dry bakery blend, a wet bakery blend, a meat alternative, a dairy alternative, an alcoholic beverage, a quick bread, a cooked grain, a mixed dish, a non-meat mixed dish, a powder, a snack bar, a protein bar, a batter, a dip, or any food product suitable for consumption.

In some embodiments, the feature extractor 130 generates a new (e.g., improved, adapted, different, original) recipe for the target food product according to the ingredient rankings and/or the input data 150. In some embodiments, the feature extractor 130 incorporates (e.g., substitutes in, swaps in, replaces in, incorporates, adds, supplements, combines or otherwise uses) a select ingredient in connection with an original ingredient from an existing or available recipe. In some embodiments, the select ingredient and the original ingredient are in the same ingredient category. In some embodiments, the feature extractor 130 determines that the select ingredient has one or more properties that match, are similar to, complements or improves upon the original ingredient, and/or that the select ingredient has a higher/similar ingredient ranking than an original ingredient being replaced/swapped/removed. In some embodiments, the feature extractor 130 substitutes the select ingredient for the original ingredient based on the matching/similar/improved properties and the respective ingredient rankings.

The feature extractor 130 can incorporate, in the new recipe, one or more select ingredients from the ingredients included in the ingredients being ranked. In some embodiments, the feature extractor 130 has a higher probability of incorporating, as the select food ingredient, a first food ingredient than a second food ingredient with a ranking that is lower than that of the first food ingredient. In some embodiments, the select ingredient(s) include an ingredient that has a ranking that is higher than that of all the other ranked ingredients. In some embodiments, the select ingredient(s) include an ingredient that has a ranking that is lower than that of at least one ingredient included in the ranked ingredients. For instance, the select ingredient may have a lower ranking than another ingredient, but the AI driven platform may determine that the select ingredient is a better fit in the new recipe because of certain factors, limitation and/or considerations.

In some embodiments, customer/consumer/user preference data includes an indication that at least one ingredient in an existing recipe is to be included or excluded in the new recipe. For example, a first recipe may include a paste (e.g., a date paste). A tag (e.g., indicator, instruction, guidance, restriction, modifier, setting, parameter, configuration) can be used to indicate to the AI driven platform (e.g., feature extractor 130) that the paste is to be included in the final recipe (e.g., because of the consistency of the paste and/or because the paste holds the other ingredients together). In some embodiments, the feature extractor 130 receives the tag as part of the existing recipe. In some embodiments, the feature extractor 130 receives the tag separately from the existing recipe, determines that the existing recipe is to be tagged (e.g., tagged, linked, mapped, or otherwise associated) with the tag, and tags the existing recipe with the tag. In some embodiments, the feature extractor 130 determines that the tag is to be applied to the existing recipe by identifying an ingredient (or specific requirements, goals or properties in replacing/removing/using/selecting an ingredient) specified in the tag that matches an ingredient in the existing recipe (e.g., the paste) to be replaced/removed, or that matches an ingredient from the candidate list of ranked ingredients.

In some embodiments, the feature extractor 130 generates one or more new recipes at a time, or over a period of time. By way of a non-limiting example, the feature extractor 130 may generate (e.g., formulate, propose) a first new recipe. The feature extractor 130 may send (e.g., via a computer network) the first new recipe to the user/customer (e.g., a user/customer device). The feature extractor 130 may receive one or more tags in response to the first new recipe. The feature extractor 130 may generate a second new recipe based on the input data 150 including the one or more tags received in response to the first new recipe.

In some embodiments, the existing recipes and/or the new recipe may include, specify or describe the select ingredient(s), an amount of each select ingredient, a process and/or an order of steps in which to add/incorporate select ingredient(s), the step(s) to take (e.g., cook, bake, fry, freeze, chop, peel, and the like) on at least one select ingredient, and the like. The existing recipes and/or the new recipe(s) can be generated, represented, stored, described or accessed in a file (e.g., excel file, a JPEG file, a PDF file), in a memory, in a data structure, or any suitable format for representing, storing, describing, or accessing the existing recipes and/or new recipe(s).

In some embodiments, the feature extractor 130 includes or uses heuristic or rules based systems, user (e.g., customer, developer, consumer) feedback, clustering (e.g., k-means clustering) and/or other algorithms, decision trees, supervised machine learning (e.g., support-vector machine), and/or a neural network (e.g., convolutional neural network). The neural network is described below with respect FIGS. 2A-2B. In some embodiments, the neural network operates in two phases: a training phase and a run time phase. The training phase is described with respect to FIG. 2B and the run time phase is described with respect to FIG. 2A.

Figure 2A:
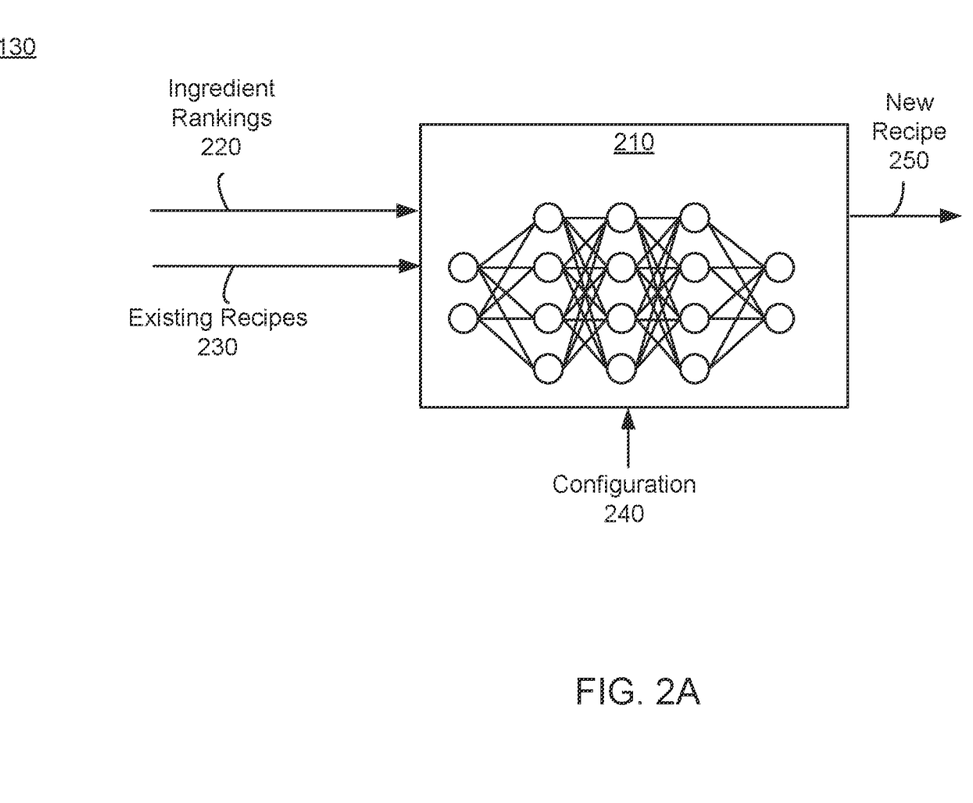
FIG. 2A is a block diagram of a neural network of a feature extractor (which may sometimes be referred as, or as part of, a recommendation engine or recipe generator), according to an example implementation of the present disclosure.

FIG. 2A is a block diagram of a neural network 210 of a feature extractor 130, according to an example implementation of the present disclosure. In some embodiments, the feature extractor 130 includes more, fewer, or different components than shown in FIG. 2A. In some embodiments, the neural network 210 receives inputs (e.g., ingredient rankings 220, existing recipes 230, ingredient property data, customer/consumer/user preference data, and/or market data). In some embodiments, the neural network 210 generates (e.g., during a runtime phase) a new recipe 250 from the inputs according to weights and/or biases of nodes of layer(s) in the neural network 210, indicated by the configuration 240.

Figure 2B:
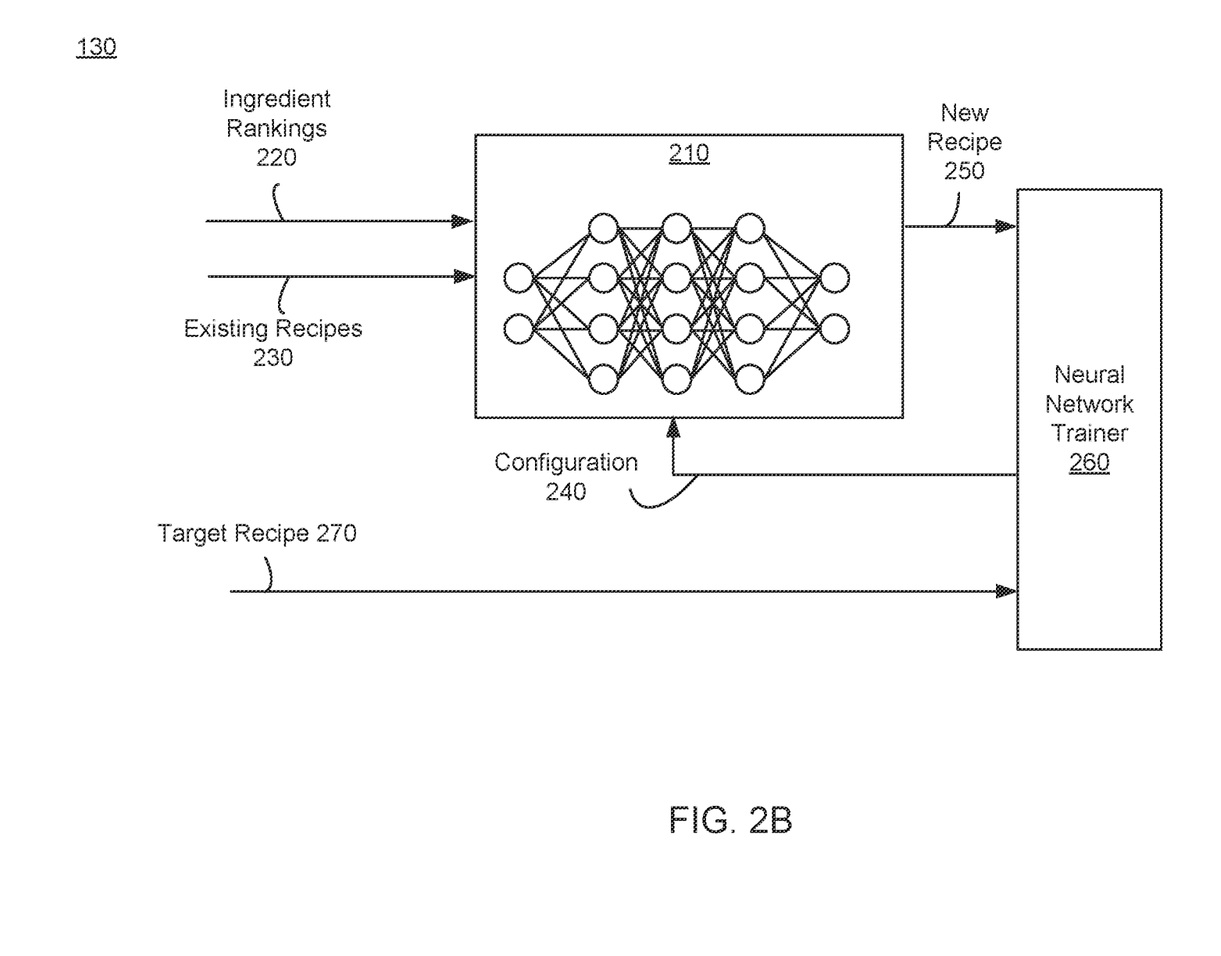
FIG. 2B is a block diagram of a neural network trainer training a neural network of a feature extractor, according to an example implementation of the present disclosure.

FIG. 2B is a block diagram of a neural network trainer 260 training a neural network 210 of a feature extractor 130, according to an example implementation of the present disclosure. In some embodiments, the feature extractor 130 includes more, fewer, or different components than shown in FIG. 2B. The neural network 210 of FIG. 2B may be similar to the neural network 210 of FIG. 2A. In a training phase for the neural network 210, the neural network trainer 260 may receive an output or new recipe 250 from the neural network 210. Moreover, the neural network trainer 260 may receive a target recipe 270 (e.g., for training the neural network), which may correspond to the inputs (e.g., ingredient rankings 220, existing recipes 230, ingredient property data, customer/consumer/user preference data, and/or market data). The target recipe 270 may provide a reference, target output or ground truth corresponding to the inputs received by the neural network 210. The neural network trainer 260 may compare the new recipe 250 with the target recipe 270, and adjust the configuration 240 (e.g., weights, biases, and so on) of the neural network 210 according to the comparison, to reduce errors or differences between the new recipe 250 and the target recipe 270. The neural network trainer 260 may continue to train, configure, tune and/or optimize the neural network, e.g., by repeating the process with the same inputs or with different inputs, and a corresponding target recipe 270, to adjust the configuration 240, until the errors of the new recipe(s) 250 output by the neural network 210 with respect to the corresponding target recipe 270 become less than a predetermined threshold (e.g., less than 1%).

Once the errors become less than the predetermined threshold, the neural network trainer 260 may store the adjusted configuration 240 generated during the training phase for use during a run time phase. In some embodiments, the neural network 210 is implemented based on a Tensorflow/Keras based model, a pytorch based model, or other models. The neural network trainer 260 may be implemented using a Tree-based Pipeline Optimization Tool (TPOT), for example.

The data received in the traininFg phase can be referred to as training data. In some embodiments, the training data includes known ingredient rankings 220, known existing recipes 230 and/or a known target recipe 270. Then, in the run time phase, different ingredient rankings 220 and different existing recipes 230 are applied to generate or output the new recipe 250. In some embodiments, the training data includes one or more input ingredients, known ranked ingredients 220, and one or more target ingredients. Each of the one or more target ingredients can correspond to a unique one of the one or more input ingredients. Then, in the run time phase, the existing recipe 230 is applied to generate the new recipe 250.

Referring back to FIG. 1, the system can include a label engine 140. In some embodiments, the label engine 140 receives the new recipe and the ingredient property data, in one or more embodiments. The label engine 140 generates a nutritional description (e.g., a nutritional label or other description) for the new recipe, in one or more embodiments. In some embodiments, the nutritional description is based on the new recipe and the ingredient property data. In some embodiments, the label engine 140 determines the ingredients (e.g., select ingredient(s) and any other ingredients) included in the new recipe. The label engine 140 can determine a serving size for the target food product (e.g., as specified in the new recipe generated for the target food product, as an input for the label engine 140, or as part of the configuration). In some embodiments, the label engine 140 determines an amount of each ingredient in one serving of the target food product. The label engine 140 can determine the amounts of nutrients (e.g., nutritional components, such as vitamins, minerals, salt/sodium, cholesterol, carbohydrates, fats, proteins, fiber, amino acids, or others) in each ingredient for the new recipe, based on the amount of a corresponding ingredient in one serving and the ingredient property data (e.g., multiply ingredient nutrient per nominal amount, with a ratio of nominal amount and serving amount). The ingredient property data can specify or provide the amounts of nutrients in each ingredient. For each nutrient, the label engine 140 can determine a total amount of a nutrient by adding the amount of the nutrient from each ingredient, according to the ingredient property data. In some embodiments, the label engine 140 generates the nutritional description based on each nutrient and the total amount (or percentage of recommended daily intake) of the nutrient in one serving of the new recipe.

Figure 3:
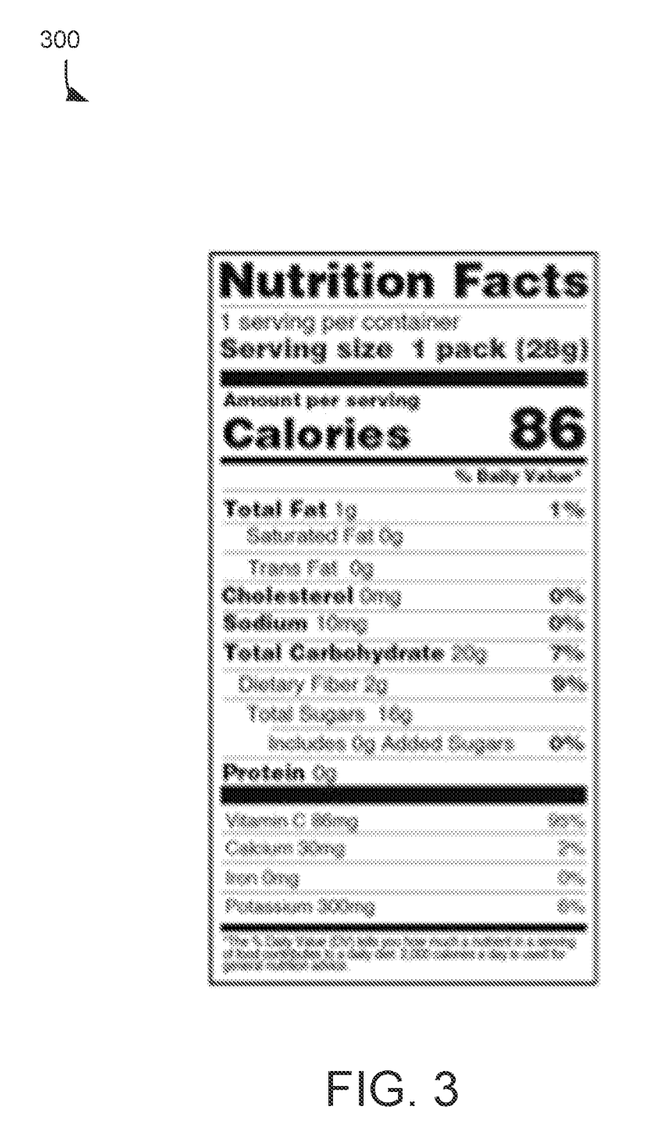
FIG. 3 shows an example nutritional description, according to an example implementation of the present disclosure.

FIG. 3 shows an example nutritional description 300, according to an example implementation of the present disclosure. The nutritional description 300 can for instance include each nutrient and an amount or percentage of the daily recommended intake of the nutrient. The label engine 140 can generate a human readable representation of the nutritional description 300 such as an excel file, a JPEG file, a PDF file, or the like. The nutritional description 300 can be displayed on a mobile device, a desktop device, or any suitable computer device.

Figure 4:
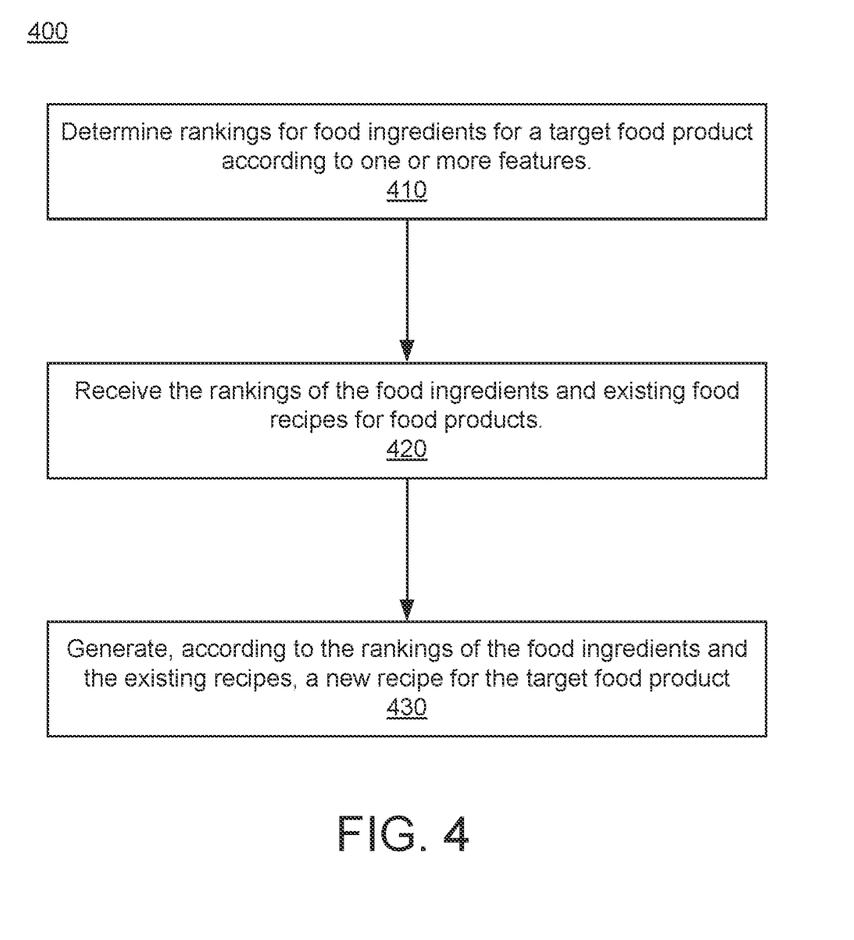
FIG. 4 is a flow chart illustrating a process of generating recipes, according to an example implementation of the present disclosure.

FIG. 4 is a flow chart illustrating a process 400 of generating recipe(s), according to an example implementation of the present disclosure. In some embodiments, the process 400 is performed by the recipe generator 100. In some embodiments, the process 400 is performed by other entities. In some embodiments, the process 400 includes more, fewer, or different steps than shown in FIG. 4. In brief overview, the recipe generator determines rankings for food ingredients for a target food product according to one or more features (410). The recipe generator receives the rankings of the food ingredients and existing food recipes for food products (420). The recipe generator generates, according to the rankings of the food ingredients and the existing recipes, a new recipe for the target food product (430).

In some embodiments, a recipe generator, such as the recipe generator 100, filters ingredients from an initial set of ingredients. The recipe generator can filter ingredients based on customer/consumer/user preference data (e.g., ingredient tags or customer/user-defined categories). In some embodiments, the recipe generator filters ingredients to retain or obtain those that are in a same category as a target food product. In some embodiments, the recipe generator filters ingredients such that a total number of the filtered ingredients is less than a predefined threshold.

In some embodiments, the recipe generator determines rankings for food ingredients for a target food product according to one or more features (410). The features may include a health-based feature (e.g., functional features or nutritional measures), a cost of the ingredient (e.g., cost of purchasing, cultivating, producing, sourcing, transporting, storing, maintaining, using and/or processing the ingredient), and/or a prevalence of the food ingredients (e.g., prevalence, level of usage/presence and/or popularity of the ingredient in all/similar recipes and/or food products in the market, and/or availability, scarcity or abundance of the ingredient in the market or from sources). In some embodiments, the recipe generator generates an ingredient score for each of the food ingredients and generates rankings according to the ingredient scores of the food ingredients. In some embodiments, the recipe generator assigns a first score component (e.g., value of 1) if one of the features of a food ingredient exceeds a predefined threshold or a second score component (e.g., a value of 0, or a value below 1) if the one of the features does not exceed the predefined threshold. In some embodiments, the ranking engine 120 aggregates the score components for features of a food ingredient to determine the ingredient score of the food ingredient.

In some embodiments, the recipe generator determines first rankings for the food ingredients according to at least one health-based feature of each of the food ingredients, second rankings for the subset of ingredients according to a cost of each of the food ingredients, and/or third rankings for the food ingredients according to a prevalence of each of the food ingredients. In some embodiments, the recipe generator determines the rankings for the food ingredients according to the first rankings, the second rankings and/or the third rankings. In some embodiments, the recipe generator determines the ranking for an ingredient by determining a function (e.g., an average, a weighted average, and the like) of the first ranking, the second ranking, and/or the third ranking of the food ingredients.

In some embodiments, the recipe generator receives, at a neural network such as the neural network 210, the rankings of the food ingredients and existing food recipes for food products, as inputs (420). In some embodiments, the existing recipes are (chosen to be) in a same category as the target food product. In some embodiments, the recipe generator further receives properties of each of the food ingredients (which can include candidate ingredients for the target food product, and/or ingredients in the existing recipes), including consistency, texture, flavor, taste, color, shelf-life, response to heat, and the like. In some embodiments, the recipe generator compares the properties of candidate ingredients and properties of original ingredients in existing food recipes. If the recipe generator finds matches, similarities, and/or complementary properties between the candidate ingredient(s) and original ingredient(s), the recipe generator can adapt, modify, improve or otherwise use an existing recipe, to generate a new recipe. In some embodiments, the recipe generator can for instance compare the ingredient rankings of the candidate ingredient(s) and the ingredient rankings of the original ingredient(s). In some embodiments, the recipe generator substitutes the candidate ingredient for the original ingredient responsive to the candidate ingredient having a higher ingredient ranking than that of the original ingredient, and/or responsive to the candidate ingredient having at least one food property matching (or similar to) that of the original ingredient.

The recipe generator generates, according to the rankings of the food ingredients and the existing recipes, a new recipe for the target food product (430). The recipe generator can incorporate, in the new recipe, one or more select ingredients from the food ingredients (e.g., the ranked/candidate ingredients). In some embodiments, the recipe generator has a higher probability of incorporating, as the select food ingredient, a first food ingredient than a second food ingredient with a ranking that is lower than that of the first food ingredient. In some embodiments, the select ingredient includes an ingredient that has a ranking that is higher than that of all the other ranked ingredients. In some embodiments, the select ingredient includes an ingredient that has a ranking that is lower than that of at least one ingredient included in the ranked in ingredients. The recipe generator can generate one or more new recipes. Each new recipe can include or specify corresponding ingredients (e.g., names, amount, form or preparation of the ingredient (e.g., powdered, grated, diced, dried, pureed, boiled, concentrated, dissolved, diluted)), preparation/cooking process, sequence or steps, and/or preparation/cooking conditions or microclimate (e.g., temperature level, humidity, applicable duration).

In some embodiments, the recipe generator generates a nutritional description (e.g., a nutritional label or other description) for the new recipe based on the new recipe and the ingredient property data. In some embodiments, the recipe generator determines the ingredients of the new recipe, a serving size of the target food product according to the new recipe, and an amount of each of the ingredients in one serving of the target food product.

The recipe generator can determine the nutrients (e.g., nutritional components, such as vitamins, minerals, salt/sodium, cholesterol, carbohydrates, fats, proteins, fiber, amino acids, or others) in the target food product. The recipe generator can determine a total amount of each nutrient in one serving of the target food product, and can indicate the presence or nutritional contribution of the corresponding nutrient via a weight (e.g., milligram), a contribution to the serving (e.g., percentage by weight of the nutrient relative to the total weight of the serving), a percentage of recommended daily consumption values, or any combination thereof. The recipe generator can generate a nutritional description according to any of the foregoing information.

In accordance with embodiments described herein, the recipe generator can facilitate rapid development and/or prototyping of new recipes using a curated (e.g., filtered and/or ranked) list of ingredients (e.g., selected or preferred because of health-based features, cost, prevalence and/or other factors), and can also automatically and/or conveniently provide a corresponding nutritional description of each of the new recipes (e.g., to facilitate review, assessment and/or to meet product labeling requirements).

Figure 5:
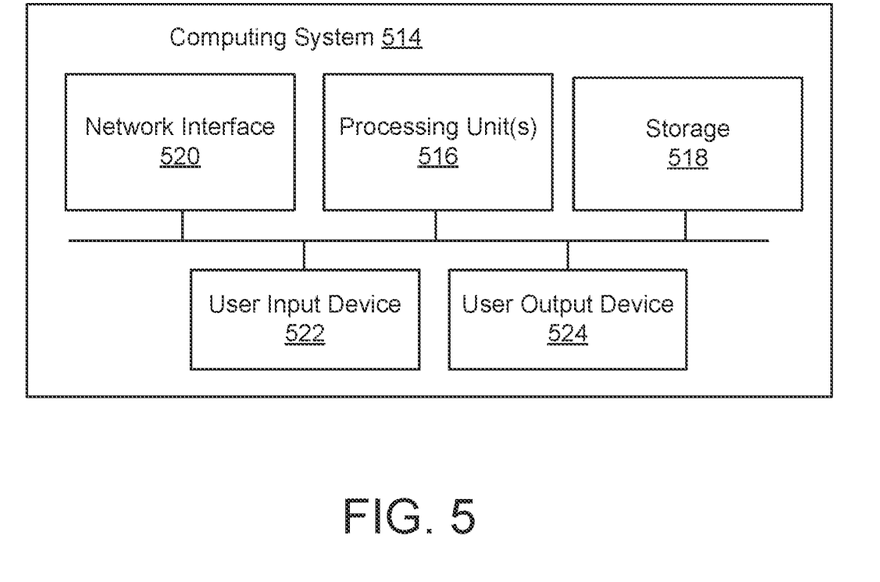
FIG. 5 is a block diagram of a computing environment according to an example implementation of the present disclosure.

Various operations described herein can be implemented on computer systems. FIG. 5 shows a block diagram of a representative computing system 514 usable to implement the present disclosure. In some embodiments, the system 100 is implemented by the computing system 514. Computing system 514 can be implemented, for example, as a consumer device such as a smartphone, other mobile phone, tablet computer, wearable computing device (e.g., smart watch, eyeglasses, head mounted display), desktop computer, laptop computer, cloud computing service or implemented with distributed computing devices. In some embodiments, the computing system 514 can include computer components such as processors 516, storage device 518, network interface 520, user input device 522, and user output device 524.

Network interface 520 can provide a connection to a wide area network (e.g., the Internet) to which WAN interface of a remote server system is also connected. Network interface 520 can include a wired interface (e.g., Ethernet) and/or a wireless interface implementing various RF data communication standards such as Wi-Fi, Bluetooth, or cellular data network standards (e.g., 3G, 4G, 5G, 60 GHz, LTE, etc.).

User input device 522 can include any device (or devices) via which a user can provide signals to computing system 514; computing system 514 can interpret the signals as indicative of particular user requests or information. User input device 522 can include any or all of a keyboard, touch pad, touch screen, mouse or other pointing device, scroll wheel, click wheel, dial, button, switch, keypad, microphone, sensors (e.g., a motion sensor, an eye tracking sensor, etc.), and so on.

User output device 524 can include any device via which computing system 514 can provide information to a user. For example, user output device 524 can include a display to display images generated by or delivered to computing system 514. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). A device such as a touchscreen that function as both input and output device can be used. Output devices 524 can be provided in addition to or instead of a display. Examples include indicator lights, speakers, tactile "display" devices, printers, and so on.

Some implementations include electronic components, such as microprocessors, storage and memory that store computer program instructions in a non-transitory computer readable storage medium. Many of the features described in this specification can be implemented as processes that are specified as a set of program instructions encoded on a computer readable storage medium. When these program instructions are executed by one or more processors, they cause the processors to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processor 516 can provide various functionality for computing system 514, including any of the functionality described herein as being performed by a server or client, or other functionality associated with message management services.

It will be appreciated that computing system 514 is illustrative and that variations and modifications are possible. Computer systems used in connection with the present disclosure can have other capabilities not specifically described here. Further, while computing system 514 is described with reference to particular blocks, it is to be understood that these blocks are defined for convenience of description and are not intended to imply a particular physical arrangement of component parts. For instance, different blocks can be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Implementations of the present disclosure can be realized in a variety of apparatus including electronic devices implemented using any combination of circuitry and software.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

In some embodiments, the ranking engine 120, the feature extractor 130, the label engine 140, the neural network 210, the neural network trainer 260, or any combination thereof, is implemented on a hardware, software, or a combination of them. The hardware and data processing components used to implement the various processes, operations, illustrative logics, logical blocks, modules and circuits described in connection with the embodiments disclosed herein may be implemented or performed with a neural network chip, a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements. Technical and scientific terms used herein have the meanings commonly understood by one of ordinary skill in the art, unless otherwise defined. Any suitable materials and/or methodologies known to those of ordinary skill in the art can be utilized in carrying out the methods described herein.

Systems and methods described herein may be embodied in other specific forms without departing from the characteristics thereof. As used herein, "approximately," "about" "substantially" or other terms of degree will be understood by persons of ordinary skill in the art and will vary to some extent on the context in which it is used. If there are uses of the term which are not clear to persons of ordinary skill in the art given the context in which it is used, references to "approximately," "about" "substantially" or other terms of degree shall include variations of +/−10% from the given measurement, unit, or range unless explicitly indicated otherwise.

Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. The orientation of various elements may differ according to other exemplary embodiments, and that such variations are intended to be encompassed by the present disclosure.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

We claim:

1. A method of generating a recipe, comprising:
   training, by a computing system, a neural network using a training dataset, the training dataset including (a) a first plurality of rankings of a first plurality of food ingredients for a first target food product and (b) a first plurality of existing recipes, each of the plurality of existing recipes including a second plurality of food ingredients;
   receiving, by the computing system, an identification of a third plurality of food ingredients for a second target food product;
   calculating, by the computing system, for each food ingredient of the third plurality of food ingredients, a plurality of scores according to a plurality of factors for ranking, the plurality of factors including at least two of: a health-based feature, a nutritional property or measure, a cost, or a prevalence of the second plurality of food ingredients;
   determining, by the computing system, a second plurality of rankings for the third plurality of food ingredients for the second target food product based at least on the plurality of scores for each food ingredient of the third plurality of food ingredients;
   identifying, by the computing system, from a database of recipes, a second plurality of existing recipes for food products in a category that is same as the second target food product;
   applying, by the computing system, as input to the neural network trained using the training dataset, (1) the second plurality of rankings of the third plurality of food ingredients for the second target food product and (2) the second plurality of existing recipes in the category that is the same as the second target food product;
   generating, by the computing system, from applying the second plurality of rankings and the second plurality of existing recipes as input to the neural network, a new recipe for the second target food product incorporating a food ingredient selected from the second plurality of food ingredients to replace at least one of the third plurality of food ingredients; and
   providing, by the computing system, output data based at least on the new recipe generated for the second target food product.

2. The method of claim 1, further comprising:
   applying, by the computing system, as input to the neural network, corresponding properties of each of the third plurality of food ingredients; and
   generating, by the computing system, from applying the neural network, according to the second plurality of rankings of the third plurality of food ingredients, the plurality of existing recipes and the corresponding properties of each of the third plurality of food ingredients, the new recipe.

3. The method of claim 1, wherein the new recipe has a higher probability of incorporating a first food ingredient than incorporating a second food ingredient with a ranking that is lower than that of the first food ingredient in the second plurality of food ingredients, as the selected food ingredient.

4. The method of claim 3, wherein the selected food ingredient has a ranking that is lower than that of at least one food ingredient in the second plurality of food ingredients.

5. The method of claim 1, further comprising tagging a first recipe of the plurality of existing recipes, to limit a type of modification to the first recipe by the neural network in generating the new recipe.

6. The method of claim 1, wherein the second target food product comprising at least one of: a snack, a baked food, a confectionery, a synthetic plant-based product, tofu product, meat or diary alternative, an energy food item, a beverage, a meal substitute, a dietary supplement, a superfood, fresh food product, a shelf-stable food, a frozen or refrigerated food, a meat product, or a dairy product.

7. The method of claim 1, further comprising generating, by the computing system, from applying the neural network, the new recipe for the second target food product that incorporates multiple food ingredients from the second plurality of food ingredients.

8. The method of claim 1, further comprising generating, by a label engine, a nutritional description for the new recipe.

9. The method of claim 1, wherein determining the second plurality of rankings comprises:
   determining first rankings for the third plurality of food ingredients according to at least one health-based feature of each of the third plurality of food ingredients;

determining second rankings for the third plurality of food ingredients according to a cost of each of the third plurality of food ingredients;

determining third rankings for the third plurality of food ingredients according to a prevalence of each of the third plurality of food ingredients; and determining the first plurality of rankings for the third plurality of food ingredients according to the first rankings, the second rankings and the third rankings.

10. The method of claim 1, wherein the health-based feature of the third plurality of food ingredients includes a nutritional measure of one of the third plurality of food ingredients.

11. A system for generating a recipe, comprising:

a neural network trained using a training dataset, the training dataset including (a) a first plurality of rankings of a first plurality of food ingredients for a first target food product and (b) a first plurality of existing recipes, each of the plurality of existing recipes including a second plurality of food ingredients; and at least one processor configured to:

train the neural network using the training dataset;

receive an identification of a third plurality of food ingredients for a second target food product;

calculate, for each food ingredient of the third plurality of food ingredients, a plurality of scores, according to a plurality of factors for ranking, the plurality of factors including at least two of: a health-based feature, a nutritional property or measure, a cost, or a prevalence of the second plurality of food ingredients;

determine a second plurality of rankings for the third plurality of food ingredients for the second target food product based at least on the plurality of scores for each food ingredient of the third plurality of food ingredients;

identify, from a database of recipes, a second plurality of existing recipes for food products in a category that is same as the second target food product;

apply, as input to the neural network trained using the training dataset, (1) the second plurality of rankings of the third plurality of food ingredients for the second target food product and (2) the second plurality of existing recipes in the category that is the same as the second target food product;

generate, from applying the second plurality of rankings and the second plurality of existing recipes to the plurality of weights of the neural network, a new recipe for the second target food product incorporating a food ingredient selected from the second plurality of food ingredients to replace at least one of the third plurality of food ingredients; and provide output data based at least on the new recipe generated for the second target food product.

12. The system of claim 11, wherein the is configured to:

apply, as input to the neural network, corresponding properties of each of the third plurality of food ingredients; and generate, from applying the neural network, according to the first plurality of rankings of the third plurality of food ingredients, the plurality of existing recipes and the properties of each of the third plurality of food ingredients, the new recipe.

13. The system of claim 11, wherein the new recipe has a higher probability of incorporating a first food ingredient than incorporating a second food ingredient with a ranking that is lower than that of the second food ingredient in the first plurality of food ingredients, as the selected food ingredient.

14. The system of claim 13, wherein the selected food ingredient has a ranking that is lower than that of at least one food ingredient in the first plurality of food ingredients.

15. The system of claim 11, wherein the at least one processor is configured to tag a first recipe of the plurality of existing recipes, to limit a type of modification to the first recipe by the neural network in generating the new recipe.

16. The system of claim 11, wherein the second target food product comprises at least one of: a snack, a baked food, a confectionery, a synthetic plant-based product, tofu product, meat or diary alternative, an energy bar, a beverage, a meal substitute, a dietary supplement, a superfood, fresh food product, a shelf-stable food, a frozen or refrigerated food, a meat product, or a dairy product.

17. The system of claim 11, wherein the at least one processor is configured to generate, from applying the neural network, the new recipe to incorporate multiple food ingredients from the first plurality of food ingredients.

18. The system of claim 11, further comprising a label engine implemented by the at least one processor, configured to generate a nutritional description for the new recipe.

19. The system of claim 11, the at least one processor is configured to:

determine first rankings for the third plurality of food ingredients according to at least one health-based feature of each of the third plurality of food ingredients;

determine second rankings for the third plurality of food ingredients according to a cost of each of the third plurality of food ingredients;

determine third rankings for the third plurality of food ingredients according to a prevalence of each of the third plurality of food ingredients; and determine the first plurality of rankings for the third plurality of food ingredients according to the first rankings, the second rankings and the third rankings.

20. The system of claim 11, wherein the health-based feature of the third plurality of food ingredients includes a nutritional measure of one of the third plurality of food ingredients.

* * * * *